US00PP17099P2

(12) United States Plant Patent
Zary

(10) Patent No.: US PP17,099 P2
(45) Date of Patent: Sep. 12, 2006

(54) GRANDIFLORA ROSE PLANT NAMED 'JACZEYEL'

(50) Latin Name: *Rosa hybrida*
Varietal Denomination: JACzeyel

(75) Inventor: Keith W. Zary, Agoura Hills, CA (US)

(73) Assignee: Jackson & Perkins Wholesale, Inc., Medford, OR (US)

( * ) Notice: Subject to any disclaimer, the term of this patent is extended or adjusted under 35 U.S.C. 154(b) by 0 days.

(21) Appl. No.: 11/139,322

(22) Filed: May 27, 2005

(51) Int. Cl.
*A01H 5/00* (2006.01)

(52) U.S. Cl. ..... Plt./134
(58) Field of Classification Search ..... Plt./134
See application file for complete search history.

*Primary Examiner*—Kent Bell
*Assistant Examiner*—June Hwu
(74) *Attorney, Agent, or Firm*—Klarquist Sparkman LLP

(57) ABSTRACT

Grandiflora rose plant having clear, yellow flowers having light, spicy fragrance; blooms presented in large open clusters; propagated easily from softwood cuttings; dark, semi-glossy foliage, and resistant to powdery mildew and rust.

1 Drawing Sheet

Genus and species: *Rosa hybrida.*
Variety denomination: 'JACzeyel'.

ORIGIN OF THE INVENTION

The present invention relates to a new and distinct variety of a grandiflora rose plant named 'JACzeyel' which was originated by me by crossing an unnamed, unpatented yellow hybrid tea seedling, (AROkish, U.S. Plant Pat. No. 6,796×JACjel, U.S. Plant Pat. No. 4,438 (also known as 'Sunbright')) with an unnamed, unpatented red floribunda seedling (KORlima, not patented (also known as 'Lilli Marleen')×TANweieke, U.S. Plant Pat. No. 4,844 (also known as 'Showbiz')).

BACKGROUND OF THE INVENTION

The primary objective of this breeding was to produce a new rose variety having the yellow flower color, flower size and petal count of the female parent combined with the disease resistance of the male parent.

BRIEF SUMMARY OF THE INVENTION

The objective was substantially achieved, along with other desirable improvements, as evidenced by the following unique combination of characteristics that are outstanding in the new variety and that distinguish it from its parents, as well as from all other varieties of which I am aware:

1. Light, spicy fragrance.
2. Clear, yellow flower color.
3. Blooms presented in large open clusters.
4. Propagates easily from softwood cuttings.
5. Dark, semi-glossy foliage, resists powdery mildew and rust.

Asexual reproduction of this new variety by cuttings, as performed at Wasco, Calif., shows that the foregoing and all other characteristics and distinctions come true to form and are established and transmitted through succeeding propagations.

Comparison with Parents

'JACzeyel' differs from the female parent in that the flowers are lighter yellow, are presented more frequently in clusters and the plants are more compact. Compared to the male parent, flowers are completely different in color, plants are much taller and flowers have many more petals.

Comparison with Similar Variety

The closest variety to 'JACzeyel' is 'JACjel' (U.S. Plant Pat. No. 4,438) (Sunbright). 'JACzeyel' has more clusters, greater disease resistance, lighter yellow flowers, and is more compact.

BRIEF DESCRIPTION OF THE ILLUSTRATION

The accompanying illustration shows typical specimens of the vegetative growth and flowers of this new variety in different stages of development, depicted in color as nearly true as it is reasonably possible to make the same in a color illustration of this character.

DETAILED BOTANICAL DESCRIPTION

The following is a detailed description of my new rose cultivar with color descriptions using terminology in accordance with The Royal Horticultural Society (London) Colour Chart© 2001, except where ordinary dictionary significance of color is indicated.

Parentage:

*Seed parent.*—Unnamed yellow hybrid tea seedling (not patented) (AROkish×JACjel).

*Pollen parent.*—Unnamed red floribunda seedling (not patented) (KORlima×TANweieke).

FLOWER

Observations made from January 2003 to September 2004 from plants commencing at three years of age grown in a garden environment at Somis, Calif.

Blooming habit: Continuous.

Bud:

*Size.*—About 4 cm long and 3 cm in diameter when the petals start to unfurl.

*Form.*—The bud form is long, pointed ovoid.

*Color.*—When sepals first divide, bud color is Yellow Group 3B. When half blown, the upper sides of the petals are Yellow Group 3B and the lower sides of the petals are Yellow Group 3B.

*Sepals.*—Color: Upper surface: Green Group 138B often blushed with Greyed-Red Group 184A. Lower surface: Green Group 137D. Length: 30–32 mm. Width: 9–10 mm. Shape: Subulate. Upper Surface texture: Hoary. There are three normally appendaged sepals. There are two unappendaged sepals with hairy edges.

*Receptacle.*—Color: Green Group 137C. Shape: Funnel. Size: Medium, about 10 mm long×7 mm wide. Surface: Smooth.

*Peduncle.*—Length: Short, averaging about 40 mm. Surface: Glandular. Color: Yellow-Green Group 146B. Strength: Stiff, erect.

Bloom:

*Size.*—Medium. Average open diameter is about 10 cm.

*Borne.*—Several together in flat clusters of 3–5 blooms.

*Stems.*—Strength: Strong. Average length is about 40–45 cm with a diameter of 7–8 mm.

*Form.*—When first open: High centered. Permanence: Flattens, outer petals curl back.

*Petalage.*—Number of petals under normal conditions: 40–45.

*Color.*—The upper sides of the petals are Yellow Group 3B changing to Yellow Group 3C on the petal edges. The reverse sides of the petals are Yellow Group 3B. The base of the petals has a small (2 mm×2 mm) Yellow Group 3A color spot. The major color on the upper side is Yellow Group 3B.

*Variegations.*—None observed.

*Discoloration.*—The general tonality at the end of the first day: No change. At the end of the third day: No change. Further aging: Day 4 or 5 there is a color change to Yellow Group 3D.

*Fragrance.*—Moderate, spicy.

Petals:

*Texture.*—Thick, leathery.

*Shape.*—Round.

*Surface.*—Smooth.

*Margin.*—Entire. Apex Shape: Rounded. Base Shape: Rounded.

*Form.*—Tips slightly recurved.

*Arrangement.*—Imbricated.

*Petaloids.*—Number: 3 to 5, ranging in size from 5 mm×20 mm to 10×25 mm. Color: Yellow Group 3B.

*Persistence.*—Petals drop off cleanly before drying.

*Lastingness.*—On the plant: Long (about 7–8 days). As a cut flower: Long (about 9–10 days).

Reproductive parts:

*Stamens.*—Number: 50–60. Length: 7–8 mm. Anthers: Length: 2–3 mm. Color: Yellow-Orange Group 15D. Arrangement: Regular around styles. Filaments: Color: Red Group 47A. Length: 5–6 mm. Pollen: Color: Yellow-Orange Group 22A.

*Pistils.*—Number: 40–45. Length: 9–10 mm. Styles: Color: Green-White Group 157A. Length: 8–9 mm. Stigmas: Color: Greyed-Yellow Group 160D. Length: 1 mm.

*Hips.*—None observed.

PLANT

*Form.*—Bush.

*Growth.*—Vigorous, upright, branching.

*Age at maturity.*—Two years.

*Mature plant.*—Height: 150 cm. Width: 100 cm.

*Rootstock.*—Own root.

Foliage: Number of leaflets on normal mid-stem leaves: 5 or 7.

*Size.*—Large. About 15 cm long×13 mm wide.

*Quantity.*—Abundant.

*Color.*—New foliage: Upper side: Greyed-Purple Group 183B. Lower side: Greyed-Purple Group 183B. Old foliage: Upper side: Green Group 139A. Lower side: Green Group 138A.

Leaflets:

*Size.*—About 6 cm long×3.5 cm wide.

*Shape.*—Pointed oval.

*Base shape.*—Oblique.

*Apex shape.*—Acuminate.

*Texture.*—Leathery, glossy.

*Edge.*—Serrated.

*Serrations.*—Single.

*Petiole.*—Color: Green Group 138C.

*Petiole rachis.*—Color: Green Group 138C. Underside: Rough with prickles.

*Auricle shape, if present.*—None.

*Stipules.*—Length: 15 mm. Edged in glands.

*Disease resistance.*—Resistant to rust and powdery mildew and susceptible to blackspot and downy mildew under normal growing conditions.

*Pest resistance.*—Not observed.

*Vein color.*—Green Group 138A.

*Venation pattern.*—Reticulate.

Wood:

*New wood.*—Color: Greyed-Purple Group 183C. Bark: Smooth.

*Old wood.*—Color: Green Group 137A. Bark: Smooth.

Prickles:

*Quantity.*—On main canes from base: 13 to 17 per 15 cm. On laterals from main canes: 13–17 per 15 cm.

*Form.*—Hooked slightly downward.

*Length.*—

*Color when young.*—Greyed-Purple Group 183A.

*Color when mature.*—Greyed-Orange Group 166D.

Small prickles:

*Quantity.*—On main stalks: None. On laterals: None.

Winter hardiness: Hardy to Zone 5.

I claim:

1. A new and distinct variety of rose plant of the grandiflora class, substantially as herein shown and described, characterized particularly by the light, spicy fragrance and clear, yellow color of its flowers; blooms presented in large open clusters; ability to propagate easily from softwood cuttings; its dark, semi-glossy foliage, and resistance to powdery mildew and rust.

* * * * *

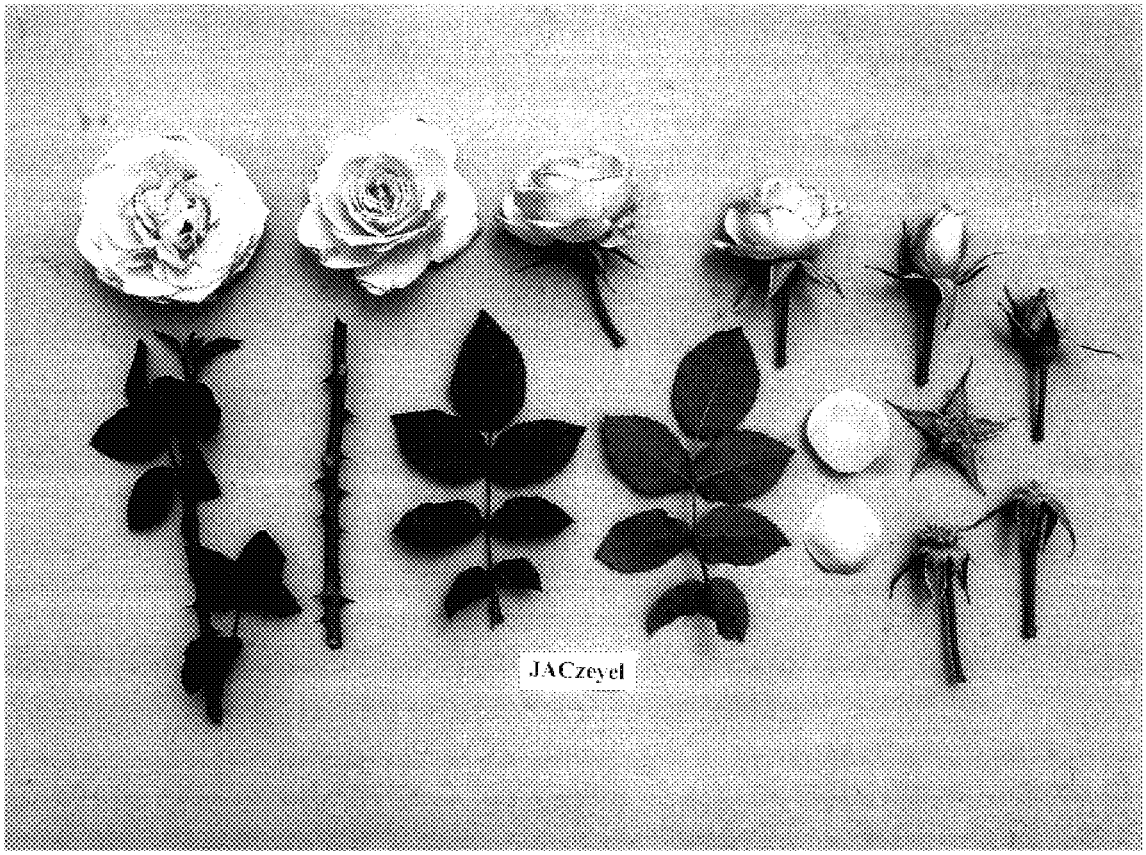
JACzeyel